United States Patent [19]

Yoshimoto et al.

[11] Patent Number: 4,734,493

[45] Date of Patent: Mar. 29, 1988

[54] NOVEL ANTHRACYCLINE ANTIBIOTICS

[75] Inventors: Akihiro Yoshimoto, Fujisawa; Osamu Jodo, Yokohama; Yoshio Watanabe, Fujisawa; Tomoyuki Ishikura, Chigasaki; Tsutomu Sawa, Ayase; Tomio Takeuchi; Hamao Umezawa, both of Tokyo, all of Japan

[73] Assignee: Sanraku, Incorporated, Tokyo, Japan

[21] Appl. No.: 849,229

[22] Filed: Apr. 7, 1986

[30] Foreign Application Priority Data

Apr. 12, 1985 [JP] Japan .................................. 60-076777

[51] Int. Cl.$^4$ ............................................. C07H 15/24
[52] U.S. Cl. ..................................................... 536/6.4
[58] Field of Search ......................................... 536/6.4

[56] References Cited

U.S. PATENT DOCUMENTS

| 4,207,313 | 6/1980 | Umezawa et al. | 536/6.4 |
| 4,316,011 | 2/1982 | Oki et al. | 536/6.4 |
| 4,439,603 | 3/1984 | Umezawa et al. | 536/6.4 |

Primary Examiner—J. R. Brown
Assistant Examiner—Elli Peselev
Attorney, Agent, or Firm—Jordan and Hamburg

[57] ABSTRACT

The antibiotics designated obelmycins exhibit high proliferation inhibiting action against leukemia cells and are effective as anti-cancer agents.

5 Claims, No Drawings

NOVEL ANTHRACYCLINE ANTIBIOTICS

FIELD OF THE INVENTION

The present invention relates to novel anthracycline antibiotics produced by microorganisms belonging to the genus Streptomyces.

BACKGROUND OF THE INVENTION

As anthracycline antibiotics there are hitherto known daunomycin (cf. U.S. Pat. No. 3,616,242) and adriamycin (cf. U.S. Pat. No. 3,590,028) obtained from culture solutions of Actinomyces. These compounds exhibit broad anti-tumor spectra against experimental tumors and have been widely used as cancer chemotherapy agents also for clinical purposes. However, daunomycin and adriamycin are not always satisfactory although they exhibit considerably potent anti-cancer activity. Various attempts have been made to produce analogous compounds by various means such as a fermentation method, a semisynthesis method, a method for conversion of microorganisms, etc. and some anthracycline antibiotics have additionally been proposed [for example, Published Examined Japanese Patent Application No. 34915/76 (aclacinomycins A and B), T. OKI et al., The Journal of Antibiotics, vol. 33, pages 1331 to 1340; F. Areamone, Topics in Antibiotic Chemistry, Vol. 2, pages 102 to 279, published by ELLIS HORWOOD LIMITED; Published Japanese Patent Application No. 56494/82 (4-demethoxy-11-deoxydaunomycin, etc.); Published Unexamined Japanese Patent Application No. 15299/81 (cf. rhodomycin series antibiotics) and the like]

As anthracycline antibiotics as anti-tumor agents, a variety of analogous compounds have been proposed as described above and have been widely used in part for clinical purpose and also provided in part for clinical tests.

However, none of them is satisfactory in either toxicity or anti-tumor activity. In addition, in anti-tumor agents, the results of in vitro and animal tests do not necessarily reflect anti-tumor activity of humans directly so that investigations are required from various aspects. For this reason, with respect to anthracycline antibiotics apparently evaluated as anti-tumor agents, it has been desired to propose compounds belonging to a new class.

As a result of extensive investigations with an attempt to propose more effective anthracycline antibiotics or novel compounds capable of being synthesis intermediates thereof, the present inventors have found that Streptomyces violaceus A 262 strain belonging to the rhodomycin-producing bacteria can produce novel anthracycline antibiotics and have accomplished the present invention.

SUMMARY OF THE INVENTION

The novel anthracycline antibiotics provided in the present invention are compounds represented by the general formula:

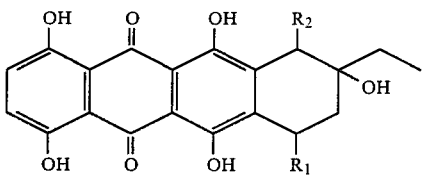

wherein $R_1$ represents a hydrogen atom or a substituent shown by the formula:

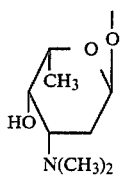

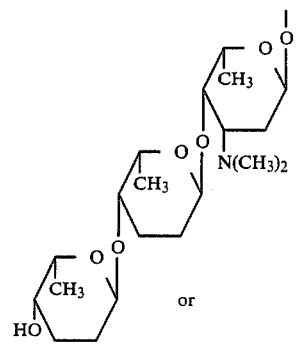

or

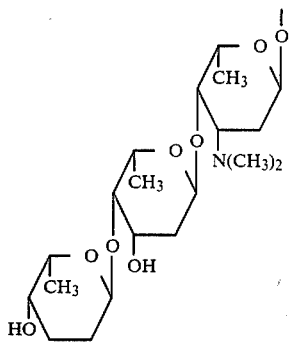

and $R_2$ represents a hydroxyl group or a group shown by the formula:

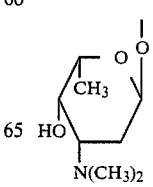

-continued

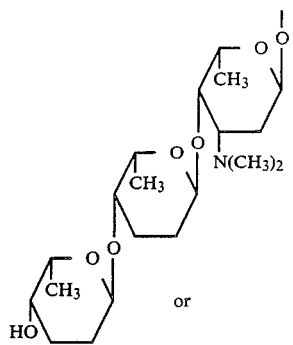

or

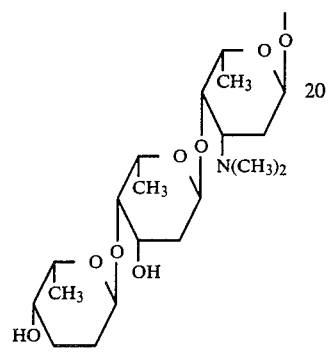

provided that when $R_1$ represents a hydrogen atom, $R_2$ represents a group other than a hydroxyl group and when $R_2$ represents a hydroxyl group, $R_1$ represents a substituent shown by the formula:

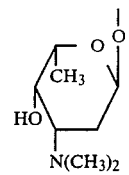

These compounds are novel antibiotics containing the β-isorhodomycinone-anthracycline skeleton that have not been recited in any prior publication.

Of the compounds represented by general formula (I), the present inventors have designated antibiotics shown by formulae (I-a), (I-b), (I-c), (I-d), (I-e), (I-f) and (I-g) as obelmycins A, B, C, D, E, F and G, respectively:

Obelmycin A: (I-a)

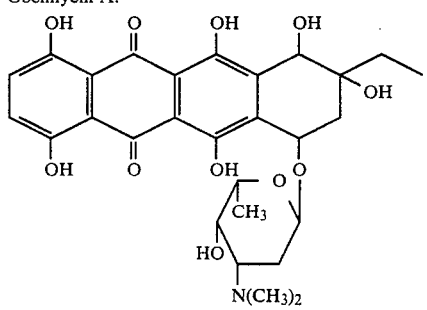

Obelmycin B: (I-b)

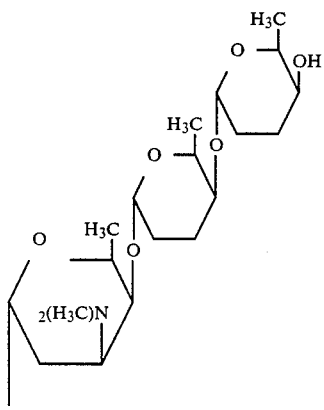

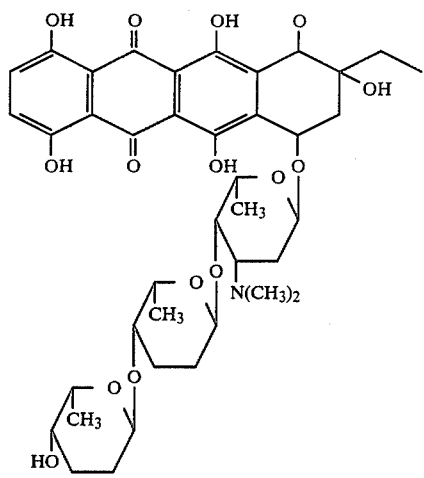
Obelmycin C: (I-c)
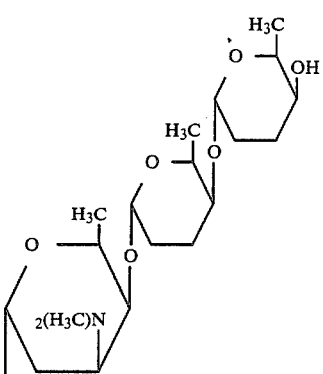
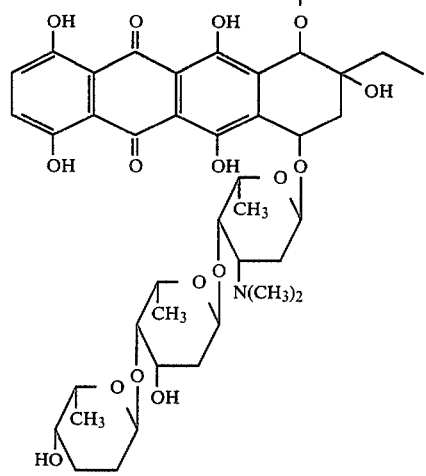
Obelmycin D: (I-d)
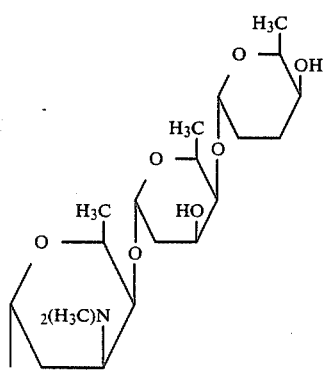

-continued
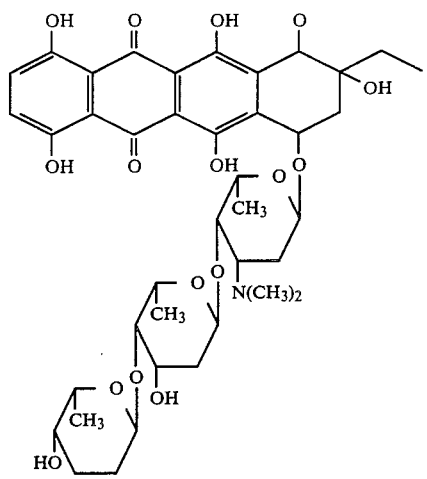
Obelmycin E:
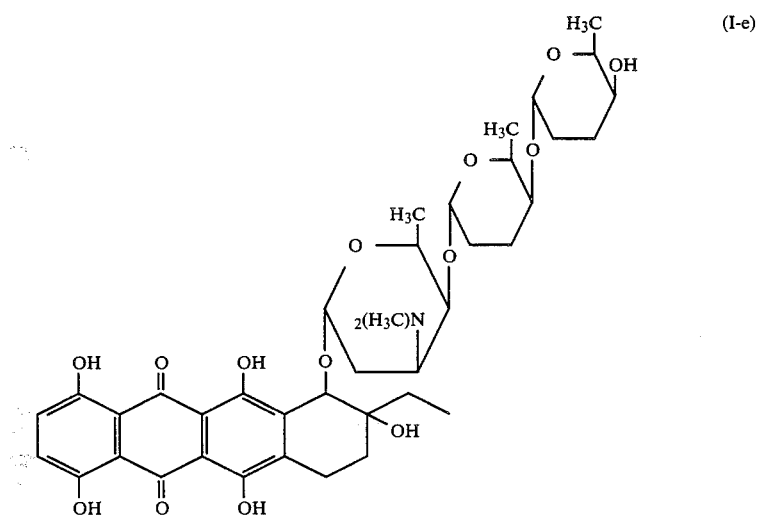
Obelmycin F:
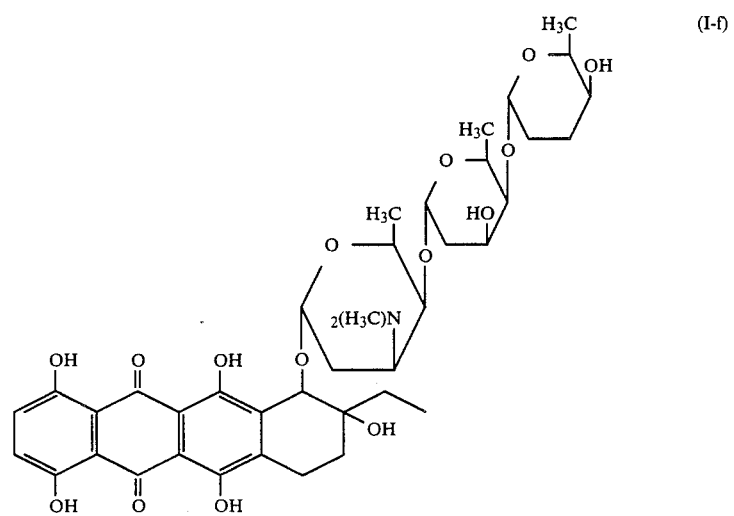
Obelmycin G:

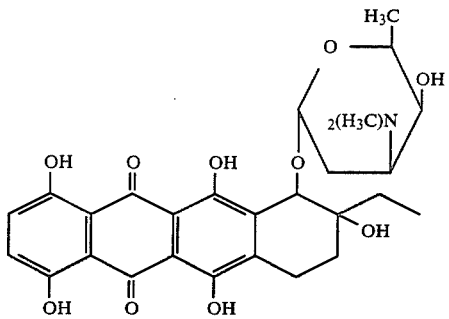 (I-g)

Hereafter the respective compounds are explained using the above nomenclature throughout the specification.

The compounds of the present invention described above possess a high degree of proliferation inhibiting action against cultured leukemia L1210 and are per se useful as anti-cancer agents.

Proliferation and nuceic acid sysnthesis inhibiting action against mouse leukemia L1210 culture cell For example, $5 \times 10^4$ ml of L1210 cells were inoculated, on RPM 11640 medium (Rosewellberg Research Institute) containing 20% bovine serum and the compound of the present invention was supplemented in a concentration of 0.0005 to 0.25 μg/ml followed by culturing at 37° C. in a carbon dioxide gas incubator. A 50% proliferation inhibiting concentration was determined as compared to control. Further the aforesaid L1210 culture cells were suspended in $8 \times 10^5$ cells/ml in RPM 11640 medium containing 10% bovine serum. After culturing at 37° C. for 1 to 2 hours in a carbon dioxide gas incubator, the compound of the present invention was supplemented in various concentrations. Fifteen minutes after, $^{14}$C-uridine (0.05 μCi/ml) or $^{14}$C-thymidine (0.05 μCi/ml) was added to the system followed by culturing at 37° C. for 60 minutes. To the reaction mixture was added chilled 10% trichloroacetic acid to discontinue the reaction. At the same time, insoluble matters were precipitated, further washed twice with chilled 5% trichloroacetic acid and then dissolved in formic acid to provide for measurement of the radioactivity. A 50% intake inhibiting concentration was determined from a rate of intake of the radioactivity in the control group added with no compound. The results are shown in Table 1.

TABLE 1

Proliferation and Nucleic Acid Synthesis Inhibiting Action of the Compounds of This Invention against Mice Leukemia L1210 Culture Cells

| Compound | 50% Inhibiting Concentration (IC$_{50}$) (μg/ml) | | |
|---|---|---|---|
| | Inhibition of Cell Proliferation | Inhibition DNA Synthesis | Inhibition RNA Synthesis |
| Obelmycin A | 0.001 | 0.58 | 0.14 |
| Obelmycin B | 0.0009 | 0.26 | 0.025 |
| Obelmycin C | 0.001 | 0.38 | 0.043 |
| Obelmycin D | 0.004 | 1.20 | 0.175 |
| Obelmycin E | 0.062 | 1.30 | 0.78 |
| Obelmycin F | 0.092 | 1.43 | 0.60 |
| Obelmycin G | 0.200 | 1.50 | 1.10 |

The therapeutic effect of obelmycins were studied on CDF$_1$ mice bearing L1210 leukemia, From 24 hours after $1 \times 10^5$ L1210 cells/animal were intraperitoneally transplanted to CDF$_1$ mice, Obelmycins were intraperitoneally given everyday for 10 days. The prolongation of the survival time was calculated relative to control animals receiving physiological saline as 100. The results are shown in Table 2.

TABLE 2

In Vivo Antitumor Activity of Obelmycins against Murine L1210 Leukemia

| Compound | optical dose (μg/kg/day) | Antitumor effect T C (%) |
|---|---|---|
| Obelmycin A | 100 | 185 |
| Obelmycin B | 3.1 | 150 |
| Obelmycin C | 3.1 | 145 |
| Obelmycin D | 3.1 | 140 |
| Obelmycin E | 12.5 | 135 |
| Obelmycin F | 25.0 | 130 |
| Obelmycin G | 200 | 145 |

Mice: CDF$_1$ n=6
Inoculation: $1 \times 10^5$ cells/mouse (ip)
Treatment: day 1 to 10, daily (ip)

The above anthracycline antibiotics can be prepared by culturing in media comprising appropriate nutrient sources bacteria producing the compounds of the present invention which can easily be isolated using bacteria isolated from the soil or known bacteria belonging to the genus Actinomycetes capable of producing rhodomycin series antibiotics or analogous compounds thereof by a conventional variation treatment using as variants, for example, ultraviolet rays or N-methyl-N'-nitro-N-nitrosoguanidine (NTG). Of these producing bacteria, a specific example include a variant, SE2-2385 strain, obtained by variation-treatment of β-rhodomycinsproducing *Streptomyces violaceus* A262 strain stored in the present inventors' Research Laboratories, with NTG.

This strain was deposited on Mar. 28, 1985 at Fermentation Research Institute, agency of Industrial Science and Technology, MITI, Japan and then transferred to international deposition under the Butapest Treaty on Mar. 26, 1986 and accorded deposit numbers FERM P-8165 and FERM BP-1004.

Hereafter bacteriological properties of SE2-2385 are shown below.

(i) Morphology

It forms helical aerial hypha from well branched substrate hypha without any whirle but with matured chain of 10 to 50 spores. The surface of the spore is thorny.

(ii) Growth conditions in various media

With respect to description of color, standard shown in parenthesis is based on Tresner & E. J. Backus, System of Color Wheels for Streptomycete Taxonomy (J. Appl. Microbiol., vol. 11, pages 335 to 338, 1963]. "Color Standard" published by Nippon Color Institute was also used supplementarily.

(iii) Growth Conditions in Respective Media (cultured at 28° C. unless otherwise indicated)

| Medium | Growth | Aerial Hypha | Substrate Hypha | Soluble pigment |
|---|---|---|---|---|
| Sucrose nitrate agar medium | Good | Hardly found, slightly white aerial hypha located locally | Deep red - dark reddish | Purple |
| Glucose aspargine agar medium | Good | Light yellowish pink (7ca) | Yellowish red - dark red | Pink |
| Glycerine aspargine agar medium | Good | Light yellowish pink (7ca) | Dark red - dark reddish purple | Purple |
| Starch inorganic salt agar medium | Good | Light yellowish pink (7ca) | Initially light yellowish pink (5ca) then reddish orange | Pink |
| Tyrosine agar medium | Good | Very pale purple (11ca) | Red - dark red | Purple |
| Nutrient agar medium | Good | Very pale purple (11ca) | Dark reddish purple | Not noted |
| Yeast maltose agar medium | Good | Pale pink at the peripheral portion | Dark red purple | Pink |
| Oatmeal agar medium | Good | Greyish yellowish pink (5cb - 6ec) | Pink | Pink |

(iv) Physiological properties (1) Growth temperature range: (examined at pH 6.0 at each temperature of 20° C., 28° C., 30° C., 37° C. and 42° C., using yeast-maltose-agar medium); Growth was noted at each temperature of 20° C. to 37° C. No growth was noted at 42° C.

(2) Liquefication of gelatin: positive (cultured at 20° C. using glucose-peptone-gelatin medium)

(3) Hydrolysis of starch: positive (starch-inorganic salts-agar medium)

(4) Coagulation of skim milk and peptonization: All were negative initially but about 15 days after culture, peptonization started.

(5) Formation of melanine-like pigment: (tryptone-yeast-broth, peptone-yeast-iron-agar and tyrosine-agar media were used); positive in any medium (v) Utilization of various carbon sources:
(Friedham-Gottlieb agar medium)

| 1. L-arabinose | positive |
|---|---|
| 2. D-xylose | positive |
| 3. D-glucose | positive |
| 4. D-fructose | positive |
| 5. sucrose | positive |
| 6. inositol | positive |
| 7. L-ramnose | positive |
| 8. raffinose | positive |
| 9. D-mannitol | positive |

The producing bacteria in accordance with the present invention can be cultured in a known medium composition conventionally used as nutrient sources for Actinomycetes. For example glucose, glycerine, sucrose, starch, maltose, animal and vegetable oils, etc. can be used as carbon sources; as nitrogen sources there may be used, for example, organic materials such as soybean powders, meat extract, yeast extract, peptone, corn steep liquor, cotton seed oil, fish powder, etc.; or inorganic nitrogens such as ammonium sulfate, ammonium chloride, sodium nitrate, ammonium phosphate, etc. If necessary and desired, sodium chloride, potassium chloride, phosphates, bivalent metal salts of $Mg^{++}$, $Ca^{++}$, $Zn^{++}$, $Fe^{++}$, $Cu^{++}$, $Mn^{++}$ or $Ni^{++}$, etc. and amino acids or vitamins can also be supplemented. In addition, in order to prevent foaming during fermentation, defoaming agents, for example, silicone (manufactured by Shin-Etsu Chemical Industry Co., Ltd., -KM 75; trademark), etc. can also be appropriately supplemented.

Conditions for fermentation such as temperature, pH, aerial agitation and fermentation time, etc. can be chosen such that the strain used can accumulate the maximum quantity of the compound. It is advantageous to conduct fermentation, for example, at temperatures of 20° to 40° C., preferably 28° C., pH of 5 to 9, preferably 6 to 7, for fermentation time of 1 to 10 days, preferably 6 days.

To isolate and collect the obelmycin substances from the culture solution, the culture after completion of the fermentation is separated into the mycelial cells and the supernatant or the filtrate by centrifugation or by filtering in the presence of appropriate filtering aids such as diatomaceous earth, etc. From the supernatant, the product is extracted with organic solvents such as chloroform, toluene, ethyl acetate, n-butanol, etc., at pH of 7 to 9.

From the mycelial caks, the product is extracted, if necessary, using organic solvents such as acetone, methanol, ethanol, butanol, etc. Each extract is concentrated to dryness to obtain crude purple powders. Either by treating the powders by chromatography using adsorption carriers, for example, synthetic adsorptive resins or silica gel, or by using treatments with anionic ion exchange resins and cationic ion exchange resins singly or in appropriate combination thereof, the obelmycin substances can be collected in their pure forms, respectively.

Hereafter the present invention will be described in more detail with reference to the examples below.

EXAMPLE 1

One platinum loop of the slant culture of YS (0.3% yeast extract, 1% soluble starch, 1.5% agar; pH 7.2) of *Streptomyces violaceus* A 262 SE2-2385 (deposited under Accession Number FERM P-8165 in the Fermentation Industry Institute) was harvested and inoculated in an Erlenmeyer's flask of a 500 ml volume separately charged with 100 ml each of seed medium described below and sterilized. Shake Culture was performed at 20° C. for 2 days using a rotary shaker (220 rpm) to prepare seed.

Seed Medium

| Soluble starch | 0.5% |
|---|---|
| Glucose | 0.5% |
| Esusan Meat (soybean powders, made by Ajinomoto Ltd.) | 1.0% |
| Yeast extract | 0.1% |
| Table salt | 0.1% |
| Potassium diphosphate | 0.1% |
| Magnesium sulfate (containing 7H$_2$O) | 0.1% |
| Tap water | 0.1% |
| pH 7.4 (Prior to sterilization) | |

Then 15 liters of production medium having the following composition were charged and 750 ml each (corresponding to 5%) of the aforesaid seed culture solution was supplemented in two jar fermenters, each having a volume of 30 liters to inoculate.

Production Medium

| Esan Meat (made by Ajinomoto Ltd.) | 2.5% |
|---|---|
| Soluble starch | 4.0% |
| Yeast extract | 0.1% |
| Table salt | 0.25% |
| Calcium carbonate | 0.3% |
| Mineral mixture* | 0.2% |
| Tap water to make 15 liters. | |
| pH 8.2 (prior to sterilization) | |

*solution of 2.8 g of CuSO$_4$.5H$_2$, 0.4 g of FeSO$_4$.7H$_2$O, 3.2 g of MnCl$_2$.4H$_2$O and 0.8 g of ZnSO$_4$.2H$_2$O in 500 ml of distilled water The system was cultured at 28° C. for 100 hours in an aeration amount of 15 liters/min. with stirring at 300 rpm, whereby the culture solution exhibited dense purple color because of the product. The culture solutions were collected from the jar fermenters and 2% of a filtering aid was added thereto followed by filtration. To the cell fraction were added 10 liters of acetone. The mixture was agitated for 20 minutes to effect extraction. Filtration was performed and the acetone extract was taken and concentrated to approximately 3 liters under reduced pressure. After the pH was adjusted to 8.5 with 4N sodium hydroxide, the system was extracted with chloroform (3 liters in total). The resultant chloroform extract was washed with water and then with a saturated saline aqueous solution and dried over Glauber's salt. After Glauber's salt was filtered off, the extract was concentrated to a small quantity under reduced pressure and n-hexane was added thereto to cause precipitation. The precipitates were filtered, collected and dried in vacuum to obtain 9.4 g of crude powders containing obelmycins A, B, C, D, E, F and G.

EXAMPLE 2

In chloroform was dissolved 5 g of the crude powders obtained in Example 1. The solution was adsorbed onto 10 g of silica gel (Wakogel C-200, manufactured by Wako Junyaku Co., Ltd.) followed by concentration to dryness. The resulting matter was put on a silica gel column (O/40 mm; 90 g of the same silica gel) filled with chloroform. Development was performed initially with a chloroform methanol (100/1) mixture (500 ml) and then the same (100/2) mixture (500 ml) to remove contaminants including aglycons. Thereafter development was further conducted with the same (100/5) mixture (1000 ml) to elute out and fractionate respective fractions containing obelmycins E, F, B, C and D in order. Then, development was performed with the same (100/10) mixture (1000 ml) to elute out and fractionate obelmycins G and A in order. Each of the fractions was concentrated to dryness to obtain partly purified powders of obelmycins A, B, C, D, E, F and G.

EXAMPLE 3

The partially purified powders of obelmycins B, C, D, E and F obtained in Example 2 were purified, respectively, using a silica gel thin layer (Silica gel 60PF254; manufactured by Merck Inc.) for fractionation. The powders were applied at the distance of 1.5 cm from the lower end of the thin layer in a horizontal line shape followed by development with a chloroform/methanol/conc. ammonia water (100/10/1). Purple isolation bands corresponding to obelmycins B, C, D, E and F were scraped off and extracted with a chloroform methanol (7/1) mixture. On the other hand, further purification of the partially purified Obelmycins A and G powders obtained in example 2 was done using a developing solvent of chloroform/methanol/conc. ammonia water (100/18/2) on preparative silica gel plates (Silica gel 60 PF$_{254}$: manufactured by Merck Inc.) The isolation bands of obelmycins A and G were scraped off and extracted with a chloroform/methanol (7/1) mixture. Each extract was concentrated to dryness and the residue was dissolved in 20 ml of a 0.1M acetate buffer (pH 3.5). The solution was extracted and washed twice with 20 ml of toluene. The aqueous layer remained after the extraction was adjusted to pH of 7.5 by adding a saturated sodium bicarbonate aqueous solution thereto and extracted with chloroform. Each chloroform extract was washed with water and dried over Glauber's salt, then filtered and concentrated under reduced pressure. Hexane was added to the residue and the mixture was stirred. The formed precipitates were filtered, collected and dried in vacuum to obtain 18, 126, 73, 42, 18, 12 and 10 mg of obelmycins A, B, C, D, E, F and G, respectively.

Physiochemical properties of obelmycins A, B, C, D, E, F and G obtained in accordance with the present invention are shown below.

Obelmycin A

Form: purple powders,
Melting point: 191°~194° C. (decomposed),
Molecular weight: 559 (measured by FD mass),
Specific rotary power: $[\alpha]_D^{23}+682°$, (c=0.004, chloroform).
UV and visible absorption spectra:

| Solvent | $\lambda$max · nm($E_{1cm}^{1\%}$) |
|---|---|
| 90% Methanol | 206(233), 241(387), 298(116), 492s(181), 523(274), 550(263), 562(275) |
| 0.01 N Hydrochloric acid-90% methanol | 206(232), 240(386), 297(117), 492s(189), 523(282), 550(267), 562(277) |
| 0.01 N Sodium hydroxide-90% methanol | 209(358), 243(386), 284(111), 586(268), 628(266) |

IR(KBr) cm$^{-1}$: 3400, 2920, 1590, 1450, 1300, 1190, 1010, 980, 790, $^1$H-NMR spectrum (CDCl$_3$): δ ppm, 1.13(t, 3H), 1.41(d, 3H), 1.75(m, 4H), 2.12(dd, 1H), 2.21(s, 6H), 2.26(d, 1H), 3.71(s, 1H), 4.08(q, 1H), 4.08(s, 1H), 4.89(s, 1H), 5.14(d, 1H), 5.50(d, 1H), 7.29(s, 2H).

Obelmycin B

Form: purple powders,
Melting point: 175°~178° C. (decomposed),
Molecular weight: 1173 (measured by FD mass),
Specific rotary power: $[\alpha]_D^{23} + 528°$, (c=0.004, chloroform).

UV and visible absorption spectra:

| Solvent | $\lambda max \cdot nm(E_{1cm}^{1\%})$ |
| --- | --- |
| 90% Methanol | 205(233), 242(354), 306(76), 364(149), 496s(92), 525(157), 553(156), 564(162) |
| 0.01 N Hydrochloric acid-90% methanol | 205(255), 241(361), 306(87), 364(173), 495s(99), 525(165), 552(160), 563(163) |
| 0.01 N Sodium hydroxide-90% methanol | 209(355), 245(355), 270s(135), 362(151), 594(161), 636(163) |

IR(KBr) cm$^{-1}$: 3450, 2920, 1580, 1450, 1300, 1190, 1000, 795, $^1$H-NMR spectrum (CDCl$_3$): δ ppm, 1.1(b, 3H), 2.21(s, 6H), 3.5(bs, 2H), 3.62(bs, 2H), 3.8(s, 1H), 3.9~4.3(m, 4H), 4.3~4.7(q, 2H), 4.89(bs, 2H), 5.0(bs, 2H), 5.10(s, 1H), 5.2(1H), 5.5(bs, 1H), 5.58(bs, 1H), 7.36(s, 2H).

Obelmycin C

Form: purple powders,
Melting point: 182°~185° C. (decomposed),
Molecular weight: 1189 (measured by FD mass),
Specific rotary power: $[\alpha]_D^{23} + 788°$ (c=0.004, chloroform).

UV and visible absorption spectra:

| Solvent | $\lambda max \cdot nm(E_{1cm}^{1\%})$ |
| --- | --- |
| 90% Methanol | 207(295), 242(422), 326(139), 496s(92), 525(156), 533(153), 564(158) |
| 0.01 N Hydrochloric acid-90% methanol | 208(324), 242(430), 325(164), 494s(100), 525(163), 553(158), 563(161) |
| 0.01 N Sodium hydroxide-90% methanol | 209(408), 244(427), 322(166), 591(157), 633(164) |

IR(KBr) cm$^{-1}$: 3400, 2920, 1580, 1450, 1300, 1190, 990, 790, $^1$H-NMR spectrum (CDCl$_3$): δ ppm, 1.1(t, 3H), 2.21(s, 6H), 3.5(b, 1H), 3.65(b, 1H), 3.8(b, 3H), 3.9~(m, 5H), 4.3~(m, 2H), 4.9(bs, 2H), 5.0(sb, 1H), 5.10(s, 2H), 5.2(bs, 1H), 5.5(bs, 2H) 7.37(s, 2H).

Obelmycin D

Form: purple powders
Melting point: 184°~187° C. (decomposed)
Molecular weight: 1205 (measured by FD mass)
Specific rotary power: $[\alpha]_D^{23} + 815°$ (c=0.004, chloroform).

UV and visible absorption spectra:

| Solvent | $\lambda max \cdot nm(E_{1cm}^{1\%})$ |
| --- | --- |
| 90% Methanol | 205(124), 242(319), 301(51), 497s(87), 525(147), 552(144), 564(149) |
| 0.01 N Hydrochloric acid-90% methanol | 206(157), 242(338), 301(73), 494s(96), 525(152), 553(147), 564(149) |
| 0.01 N Sodium hydroxide-90% methanol | 207(339), 244(312), 282(51), 594(143), 635(148) |

IR(KBr) cm$^{-1}$: 3400, 2920, 1580, 1450, 1300, 1190, 1000, 800, $^1$H-NMR spectrum (CDCl$_3$): δ ppm, 1.1(t, 3H), 2.20(s, 6H), 3.6(bs, 2H), 4.4~4.7(m, 2H), 4.90(bs, 2H), 5.08(s, 2H), 5.22(bs, 1H), 5.5(bs, 2H), 7.37(s, 2H).

Obelmycin E

Form: purple powders,
Melting point: 148°~151° C. (decomposed),
Molecular weight: 771 (measured by FD mass),
Specific rotary power: $[\alpha]_D^{23} + 595°$ (c=0.008, chloroform).

UV and visible absorption spectra:

| Solvent | $\lambda max \cdot nm(E_{1cm}^{1\%})$ |
| --- | --- |
| 90% Methanol | 204(239), 242(673), 300(111), 490(180), 522(320), 549(305), 561(336) |
| 0.01 N Hydrochloric acid-90% methanol | 204(254), 242(692), 300(116), 490(180), 522(319), 550(302), 561(328) |
| 0.01 N Sodium hydroxide-90% methanol | 208(574), 245(740), 302(98), 580(288), 620(307) |

IR(KBr) cm$^{-1}$: 3400, 2920, 1580, 1450, 1305, 1190, 1000, 800, $^1$H-NMR spectrum (CDCl$_3$): δ ppm, 1.1(t, 3H), 2.27(s, 6H), 2.96(m, 2H), 3.52(bs, 1H), 3.64(bs, 1H), 3.83(bs, 1H), 3.9~(m, 2H), 4.50(q, 1H), 4.90(bs, 1H), 5.05(s, 2H), 5.48(bs, 1H), 7.30(s, 2H).

Obelmycin F

Form: purple powders,
Melting point: 160°~163° C. (decomposed),
Molecular weight: 787 (measured by FD mass),
Specific rotary power: $[\alpha]_D^{23} + 523°$ (c=0.008, chloroform).

UV and visible absorption spectra:

| Solvent | $\lambda max \cdot nm(E_{1cm}^{1\%})$ |
| --- | --- |
| 90% Methanol | 204(210), 242(592), 300(98), 491s(157), 522(280), 549(267), 561(293) |
| 0.01 N Hydrochloric acid-90% methanol | 204(215), 242(617), 300(102), 490s(158), 523(278), 549(266), 561(287) |
| 0.01 N Sodium hydroxide-90% methanol | 208(606), 244(642), 302(86), 581(249), 621(266) |

IR(KBr) cm$^{-1}$: 3400, 2930, 1580, 1450, 1305, 1190, 1000, 800, $^1$H-NMR spectrum (CDCl$_3$): δ ppm 1.1(t, 3H), 2.24(s, 6H), 2.96(m, 2H), 3.6(bs, 1H), 3.7(bs, 2H), 3.9~4.1(1H), 4.1~(m, 2H), 4.59(q, 1H), 4.94(bs, 1H), 5.06(s, 1H), 5.11(bs, 1H), 5.49(bs, 1H), 7.33(s, 2H).

Obelmycin G

Form: purple powders,
Melting point: 194°~197° C. (decomposed),
Molecular weight: 543 (measured by FD mass),
Specific rotary power: $[\alpha]_D^{23}+773°$ (c=0.008, chloroform).

Uv and visible absorption spectra:

| Solvent | $\lambda$max · nm($E_{1cm}^{1\%}$) |
|---|---|
| 90% Methanol | 207s(253), 242(765), 300(125), 490(203), 522(365), 549(351), 561(385) |
| 0.01 N Hydrochloric acid-90% methanol | 207s(246), 243(768), 300(126), 490(205), 523(362), 549(351), 560(379) |
| 0.01 N Sodium hydroxide-90% methanol | 209(565), 245(824), 302(110), 580(331), 620(354) |

IR(KBr) cm$^{-1}$: 3400, 2920, 1580, 1450, 1305, 1190, 1020, 990, 800, $^1$H-NMR spectrum (CDCl$_3$): δ ppm, 1.1(t, 3H), 1.6~(m, 7H), 2.27(s, 6H), 2.97(m, 2H), 3.75(bs, 1H), 4.02(q, 1H), 5.05(bs, 1H), 5.45(bs, 1H), 7.32(s, 2H).

While the invention has been described in detail and with reference to specific embodiments thereof, it will be apparent to one skilled in the art that various changes and modifications can be made therein without departing from the spirit and scope thereof.

What is claimed is:

1. An anthracycline antibiotic represented by the formula:

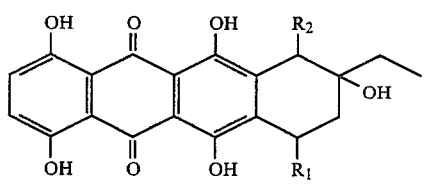
(I)

wherein R$_1$ represents a substituent shown by the formula:

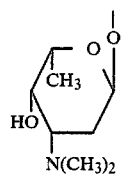
(II)

and R$_2$ represents a hydroxyl group.

2. An anthracycline antibiotic represented by the formula:

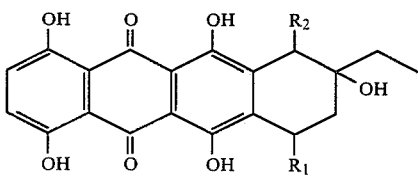
(I)

wherein R$_1$ and R$_2$ each represent a substituent shown by the formula:

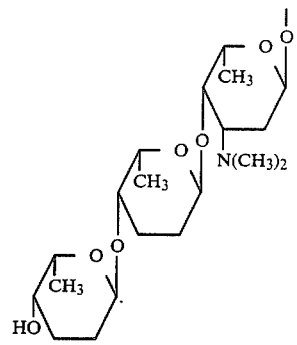
(II)

3. An anthracycline antibiotic represented by the formula:

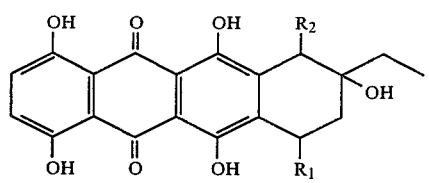
(I)

wherein R$_1$ represents a substituent shown by the formula:

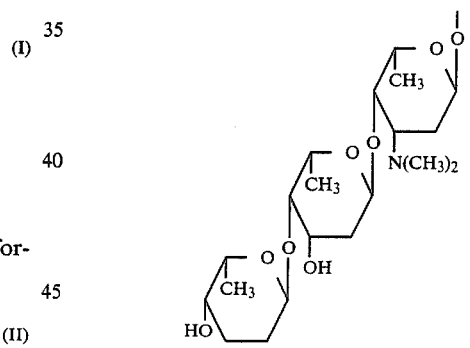
(II)

and R$_2$ represents a substituent shown by the formula:

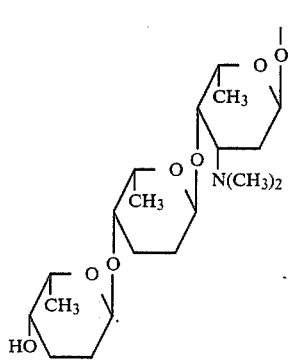
(III)

4. An anthracycline antibiotic represented by the formula:

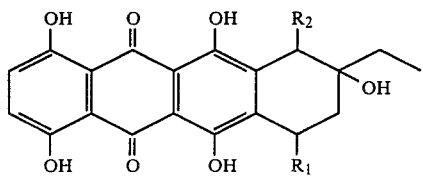
wherein $R_1$ represents a hydrogen atom and $R_2$ represents a substituent shown by the formula:
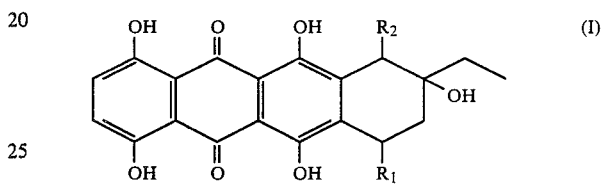
5. An anthracycline antibiotic represented by the formula:
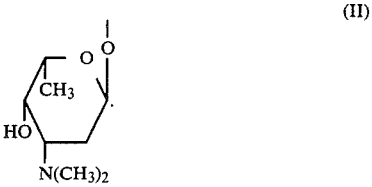
wherein $R_1$ represents a hydrogen atom and $R_2$ represents a substituent shown by the formula:
(II)
* * * * *